United States Patent [19]

Rosenblatt et al.

[11] 4,423,037

[45] Dec. 27, 1983

[54] INHIBITORS OF PEPTIDE HORMONE ACTION

[75] Inventors: Michael Rosenblatt, Newton Highlands; John T. Potts, Jr., West Newton, both of Mass.

[73] Assignee: The General Hospital Corporation, Boston, Mass.

[21] Appl. No.: 377,839

[22] Filed: May 13, 1982

[51] Int. Cl.$^3$ .................... A61K 37/00; C07C 103/52
[52] U.S. Cl. .............................. 424/177; 260/112.5 R
[58] Field of Search ................. 424/177; 260/112.5 R

[56] References Cited

U.S. PATENT DOCUMENTS 3,886,132  5/1975  Brewer et al. ...................... 424/177
4,086,196  4/1978  Tregear ......................... 260/112.5 R

OTHER PUBLICATIONS

Segre et al., Evaluation of an in vitro Parathyroid Hormone (bPTH) Antagonist in Intact Dogs, (1979), Abstract, *Calcified Tissue International*, 28(2):171.
Martin et al., An in Vitro Inhibitor of Parathyroid Hormone Action in Renal Membranes has Agonist Activity in Isolated Perfused Bone, (Apr. 1980), Journal of Clinical Research, 28(2):398A.
McGowan et al., In Vivo and in Vitro Effects of 3-34 Parathyroid Hormone (PTH), (Jul. 1981), *Journal of Clinical Research*.
Rosenblatt et al., Parathyroid Hormone Inhibitors, *Journal of Biological Chemistry*, 252(16):5847, 1977.
Goldring et al., Parathyroid Hormone Inhibitors: Comparison of Biological Activity in Bone- and Skin-Derived Tissue, *Journal of Clinical Endocrinology and Metabolism*, 48(4):655, 1979.
Segre et al., Characterization of Parathroid Hormone Receptors in Canine Renal Cortical Plasma Membranes Using a Radioiodinated Sulfur-Free Hormone Analogue, *Journal of Biological Chemistry*, 254(15):6980, 1979.
Ausiello et al., Parathyroid Hormone Modulates Protein Kinase in Giant Cell Tumors of Human Bone, *Journal of the American Physiological Society*, E144, (1980).
Rosenblatt et al., Design and Synthesis of Paratyroid Hormone Analogues of Enhanced Biological Activity, *Endocrine Research Communications*, 4(2):115, (1977).
Coltrera et al., Analogues of Parathyroid Hormone Containing D-Amino Acids: Evaluation of Biological Activity and Stability, Biochemistry, 19:4380, (1980).
Mahaffey et al., Parathyroid Hormone Inhibitors, *Journal of Biological Chemistry, 254(14):6496, (1979)*.
Rosenblatt et al., Identifiecation of a Receptor-Binding Region in Parathyroid Hormone, Endocrinology, 107(2):545, (1980).
Nussbaum et al., Parathyroid Hormone-Renal Receptor Interactions, *Journal of Biological Chemistry*, 255(21):10183, (1980).
Rosenblatt et al., Analogues of an In Vitro Parathroid Hormone Inhibitor: Modifications at the Amino Terminus, *Calcified Tissue International*, 33:153, (1981).
Rosenblatt et al., Sulfur-Free Parathyroid Hormone Analogues Containing D-Amino Acids: Biological Properties in Vitro and in Vivo, *Biochemistry*, 20:7246 (1981).
Rosenblatt, Parathyroid Hormone: Chemistry and Structure-Activity Relations, *Pathobiology Annual*, 11:53, (1981).

*Primary Examiner*—Delbert R. Phillips
*Attorney, Agent, or Firm*—Oblon, Fisher, Spivak, McClelland & Maier

[57] ABSTRACT

The present invention relates to the use of peptide hormone analogues as inhibitors of their respective naturally occurring peptide hormone. The structure of the peptide hormone analogues is exemplified by parathyroid hormone wherein the three N-terminal amino acids are removed and zero or more of the next four N-terminal amino acids are removed sequentially from the N-terminus.

64 Claims, 8 Drawing Figures

INHIBITORS OF PEPTIDE HORMONE ACTION

This work was supported in part by a grant from the National Institutes of Health

BACKGROUND OF THE INVENTION

1. Field of the Invention

This invention relates to the use of peptide hormone analogues useful in inhibiting the naturally occurring hormone peptide in vivo and in vitro. These peptide hormone analogues when administered to a vertebrate, such as mammals, fish or birds, block the endrocrine activity of the peptide hormone or other analogous molecules. These peptide hormone analogues are also useful in vitro in combination with a bioassay for the naturally occurring hormone. These peptide hormone analogues are useful in treating various diseases caused by hormone excess and in treating hormone dependent tumors. One example of this invention relates to the synthesis of parathyroid hormone analogues useful in inhibiting the action of parathyroid hormone both in vivo and in vitro.

2. Description of the Prior Art

Analysis of the relation of structure to hormonal function has provided important insights into the mechanism of action of peptide hormones. Each type of peptide hormone has an affinity for specific receptors to which it binds. Upon binding, the peptide hormone acts either directly or causes a change in the intracellular concentration of a second messenger molecule such as cyclic AMP, cyclic GMP, or calcium ions. These second messenger molecules, in turn, cause changes in the metabolism or physiology of the cell. These changes in cell metabolism or physiology are therefore directly or indirectly dependent upon the binding of the peptide hormone to its specific cell surface receptor. Therefore, if the cell surface receptor is blocked then the hormone effect is also blocked.

Peptide hormone analogues have long been known as a method through which the biochemistry of hormones can be studied and evaluated. Endocrinologists have long desired a method for producing a class of peptide hormone analogues which would allow the blocking of specific hormone receptors without activating a change in the second messenger molecules, thereby avoiding the hormone induced metabolic changes.

The following publications described the structure of peptide hormone analogues and their binding to cell receptors. In particular, these publications describe the properties of parathyroid hormone analogues and their physiological properties: (1) M. Rosenblatt, *American Society for Bone and Mineral Research, Abstract*, 1982, in press; (2) G. V. Segre, et al., *Calcified Tissue International*, 28 (2): 171, 1979; (3) K. Martin, et al., *Clinical Research*, 28 (2): 398a, April 1980; (4) J. McGowan, et al., *Central Society for Clinical Research*, 1981; (5) M. Rosenblatt, et al., *Journal of Biological Chemistry*, 252 (16): 5847, 1977; (6) S. R. Goldring, et al., *Journal of Clincal Endocrinology and Metabolism*, 48 (4): 655, 1979; (7) G. V. Segre, et al., *Journal of Biological Chemistry*, 254 (15): 6980, 1979; (8) D. A. Ausiello, et al., *American Journal of Physiology* (published by The American Physiological Society) E144, 1980; (9) M. Rosenblatt, et al., *Endrocrine Research Communications*, 4 (2): 115, 1977; (10) M. Coltrera, et al., *Biochemistry*, 19, 4380, 1980; (11) J. E. Mahaffey, et al., *The Journal of Biological Chemistry*, 254 (14): 6496, 1979; (12) M. Rosenblatt, et al., *Endocrinology*, 107 (2): 545, 1980; (13) S. R. Nussbaum, et al., *The Journal of Biological Chemistry*, 255 (21): 10183, 1980; (14) M. Rosenblatt, et al., *Calcified Tissue International*, 33, 153, 1981; (15) M. Rosenblatt, et al., *Biochemistry*, 20, 7243, 1981; (16) M. Rosenblatt, et al., *Pathobiology Annual*, 11: 53, 1981. The preceding sixteen publications are hereby incorporated by reference.

The preceding articles describe the state of the art in parathyroid hormone analogue research. Scientific efforts over a period of many years have sought to understand the interaction between peptide hormones and the cell surface receptor specific for each peptide hormone. One of the peptide hormones, parathyroid hormone has been studied by using analogues of parathyroid hormone (PTH). One objective of these studies has been to understand the binding of the peptide hormone to the cell surface receptor such that an analogue could be constructed which would bind with the same or greater affinity than the naturally occurring hormone. This analogue would enable the peptide hormone analogue of parathyroid hormone to be used to block the effect of the naturally occurring parathyroid hormone. One of the major problems encountered in this search for a clinically and pharmacologically effective parathyroid hormone analogue was the problem of agonist activity. Agonist activity is the property of the peptide hormone analogue to itself stimulate the change in second messengers which brings about the physiological change associated with the naturally occurring hormone. Therefore, the problem was to create hormone analogues which would bind with high affinity to the appropriate hormone cell surface receptor but not stimulate a change in the second messenger concentration, that is, not act as hormone itself. These analogues could then be used in treating hormone related diseases.

SUMMARY OF THE INVENTION

It is a primary object of the present invention to provide a novel method of inhibiting the action of peptide hormones through the administration of a peptide hormone or peptide hormone analogue wherein the three N-terminal amino acids are removed and from zero to four of the next four N-terminal amino acids are removed sequentially from the N-terminus.

Another object of the invention is to provide a hormone analogue comprising parathyroid hormone wherein the three N-terminal amino acids are removed and zero or more of the next four N-terminal amino acids are removed sequentially from the N-terminus.

Another object of the invention is to produce hormone analogues of bovine parathyroid hormone and human parathyroid hormone wherein the modification of the N-terminal portion of the peptide hormone results in binding to the cell surface receptor without activating the second messenger molecule.

Still another object of the invention is to produce parathyroid hormone analogues wherein the amino acid 34 is replaced by either D- or L-tyrosine.

Still another object of the present invention is to produce parathyroid hormone analogues wherein the resulting N-terminal amino acid is a D-amino acid.

Yet another object of the present invention is to produce a parathyroid hormone wherein the carboxy terminus is an amide.

An additional object of the present invention is to produce a parathyroid hormone fragment wherein amino acids 4-34 are present.

Yet another object of the present invention is to produce parathyroid hormone analogues which have one of the following structures: [L-Tyr-34] bPTH (4-34) amide, [L-Tyr-34] bPTH (5-34) amide, [L-Tyr-34] bPTH (6-34) amide, [L-Tyr-34] bPTH (7-34) amide, [D-Tyr-34] bPTH (4-34) amide, [D-Tyr-34] bPTH (5-34) amide, [D-Tyr-34] bPTH (6-34) amide, [D-Tyr-34] bPTH (7-34) amide, [Nle-8, Nle-18, Tyr-34] bPTH (4-34) amide, [L-Tyr-34] hPTH (4-34) amide, [L-Tyr-34] hPTH (5-34) amide, [L-Tyr-34] hPTH (6-34) amide, [L-Tyr-34] hPTH (7-34) amide, [D-Tyr-34] hPTH (4-34) amide, [D-Tyr-34] hPTH (5-34) amide, [D-Tyr-34] hPTH (6-34) amide, [D-Tyr-34] hPTH (7-34) amide, [Nle-8, Nle-18, Try-34] hPTH (4-34) amide.

An additional object of the invention is a method of inhibiting the action of peptide hormones through the use of a peptide hormone fragment with the three N-terminal amino acids removed and zero or more of the next four N-terminal amino acids removed sequentially from the end terminal.

Yet another object of the invention is a method of inhibiting the action of parathyroid hormone comprising the administration of therapeutically effective amount of a parathyroid hormone analogue wherein the three N-terminal amino acids are removed and zero or more of the next four N-terminal amino acids are removed sequentially from the N-terminus.

A further object of the invention is to provide a method of inhibiting the action of human parathyroid hormone comprising the administration of a thereapeutically effective amount of a human parathyroid hormone analogue wherein the three N-terminal amino acids are removed and zero or more of the next four N-terminal amino acids are removed sequentially from the N-terminus.

An additional object of the invention is a method of inhibiting the action of parathyroid hormones comprising the administration of the therapeutically effective amount of one or more of the following PTH hormone analogues: [L-Tyr-34] bPTH (4-34) amide, [L-Tyr-34] bPTH (5-34) amide, [L-Tyr-34] bPTH (6-34) amide, [L-Tyr-34] bPTH (7-34) amide, [D-Tyr-34] bPTH (4-34) amide, [D-Tyr-34] bPTH (5-34) amide, [D-Tyr-34] bPTH (6-34) amide, [D-Tyr-34] bPTH (7-34) amide, [Nle-8, Nle-18, Tyr-34] bPTH (4-34) amide, [L-Tyr-34] hPTH (4-34) amide, [L-Tyr-34] hPTH (5-34) amide, [L-Tyr-34] hPTH (6-34) amide, [L-Tyr-34] hPTH (7-34) amide, [D-Tyr-34] hPTH (4-34) amide, [D-Tyr-34] hPTH (5-34) amide, [D-Tyr-34] hPTH (6-34) amide, [D-Tyr-34] hPTH (7-34) amide, [Nle-8, Nle-18, Try-34] hPTH (4-34) amide.

Still another object of the invention is the use of a peptide hormone analogue with the three N-terminal amino acids missing and zero or more of the next four N-terminal amino acids removed sequentially from the N-terminus in an in vitro assay for peptide hormones.

Still another object of the invention is a method of treating hypercalcemia comprising the administration of a therapeutically effective amount of a parathyroid hormone wherein the three N-terminal amino acids are removed and zero or more of the next four N-terminal amino acids are removed sequentially from the N-terminus.

An additional object of the invention is a method of treating hyperparathyroidism comprising the administration of a therapeutically effective amount of the parathyroid hormone analogues of this invention.

Yet another object of this invention is a method of treating hyperparathyroidism expressed as a hypercalcemic crisis, renal failure or hypertension.

Yet another object of the present invention is a method of treating the disease state produced by a tumor or other cell overproducing a peptide hormone-like molecule.

Another object of the present invention is a method of treating immune diseases wherein the disease state comprises inflammation, an allergic response, or hyperactive lymphocytes.

The above and other objects are achieved in accordance with the present invention by providing novel peptide hormone analogues wherein the three N-terminal amino acids are removed and zero or more of the next four N-terminal amino acids are removed sequentially from the N-terminus.

BRIEF DESCRIPTION OF THE DRAWINGS

Various other objects, features and attendent advantages of the present invention will be more fully appreciated as the same becomes better understood from the following detailed description when considered in connection with the accompanying drawings.

DESCRIPTION OF THE PREFERRED EMBODIMENTS

Extensive structure and activity studies have now led to the design of peptide hormone analogues which have high binding affinity for their respective cell surface receptors while not stimulating the production of second messenger molecules. An example of such a peptide hormone analogue is [Tyr-34] bPTH (7-34) amide which inhibits PTH in vivo but does not act as an agonist. The binding to the PTH receptor is contained in the sequence of amino acids 1 through 34. Agonist activity is dependent upon the presence of the N-terminal amino acid sequence. The removal of the three end terminal amino acids results in the loss of most if not all agonist activities. Therefore, the second messenger molecules are not affected by those analogues which have the altered amino terminus.

N-terminal truncation of PTH to position 7 does not result in a complete loss of receptor binding. Therefore, PTH analogues with three to seven amino acids removed from the N-terminus produces an inhibitor which binds with high affinity to the peptide hormone receptor without causing a change in cyclic AMP concentration. The balance of the description will be divided into two sections. Section I will describe the preparation and structure of inhibitors of peptide hormones, Section II will discuss the use of the peptide hormone inhibitors.

I.

Preparation and Structure of Peptide Hormone Inhibitors

The technique of solid-phase peptide synthesis, developed by Merrifield ("Solid-Phase Peptide Synthesis", *Advances in Enzymology*, 32:221–296, 1969) has been successfully employed in the synthesis of peptide hormones including parathyroid hormone. This method is based on the strategy of having the carboxyl terminus of the peptide linked covalently to a solid support. The desired peptide sequence is prepared by stepwise coupling of single amino acids to a peptide chain growing from the carboxyl toward the amino terminus. Because each amino acid is coupled by nearly the same series of reactions, the need for elaborate strategies in the synthesis is minimized. Solublility is not a major issue during synthesis, because the peptide is linked to a solid support. This method is rapid and it can be utilized by a single worker. It is very convenient for the synthesis of multiple analogues with amino-terminal substitutions, because a single synthesis can be branched in multiple directions near the amino terminus, thereby creating many analogues varying only in the amino terminal region.

The following is the 84-amino acid sequence of bovine parathyroid hormone (bPTH): $H_2N$-ALA-VAL-SER-GLU-ILE-GLN-PHE-MET-HIS-ASN-LEU-GLY-LYS-HIS-LEU(15)-SER-SER-MET-GLU-ARG-VAL-GLU-TRP-LEU-ARG-LYS-LYS-LEU-GLN-ASP(30)-VAL-HIS-ASN-PHE-VAL-ALA-LEU-GLY-ALA-SER-ILE-ALA-TYR-ARG-ASP(45)-GLY-SER-SER-GLN-ARG-PRO-ARG-LYS-LYS-GLU-ASP-ASN-VAL-LEU-VAL(60)-GLU-SER-HIS-GLN-LYS-SER-LEU-GLY-GLU-ALA-ASP-LYS-ALA-ASP-VAL(75)-ASP-VAL-LEU-ILE-LYS-ALA-LYS-PRO-GLN-COOH.

The following is the 84-amino acid sequence of human parathyroid hormone (hPTH): $H_2N$-SER-VAL-SER-GLU-ILE-GLN-LEU-MET-HIS-ASN(10)-LEU-GLY-LYS-HIS-LEU-ASN-SER-MET-GLU-ARG(20)-VAL-GLU-TRP-LEU-ARG-LYS-LYS-LEU-GLN-ASP(30)-VAL-HIS-ASN-PHE-VAL-ALA-LEU-GLY-ALA-PRO(40)-LEU-ALA-PRO-ARG-ASP-ALA-GLY-SER-GLN-ARG(50)-PRO-ARG-LYS-LYS-GLU-ASP-ASN-VAL-LEU-VAL(60)-GLU-SER-HIS-GLU-LYS-SER-LEU-GLY-GLU-ALA(70)-ASP-LYS-ALA-ASP-VAL-ASP-VAL-LEU-THR-LYS(80)-ALA-LYS-SER-GLN-COOH.

Fragments of peptide hormones containing the region specific for binding to the cell surface receptor can be used as inhibitors or blocking agents. For parathyroid hormone, the N-terminal 34 amino acids are sufficient to define binding specificity to the parathyroid hormone cell surface receptor. This receptor specificity is further defined by the following publication herein incorporated by reference: M. Rosenblatt, et al., *Endocrinology*, 107:2, 545–550, 1980 and S. R. Nussbaum, et al., *Journal of Biological Chemistry*, 255:10183, 1980.

The presence of D-amino acids in peptide hormone in place of L-amino acids results in a peptide resistant to catabolism. However, not all such substitutions result in an active peptide hormone. The insertion of D-tyrosine at position 34 in PTH results in a significant increase in the biological activity of the hormone in addition to increasing stability of the peptide. The utilization of D-amino acids in peptide hormone synthesis is described in the following publications herein incorporated by reference: Coltrera, et al., *Biochemistry*, 19:4380–4385, 1980; Rosenblatt et al., *Biochemistry*, 20:7246–7250, 1981.

The PTH containing amino acids 4–34 was found to bind effectively to the PTH receptor without stimulating production of cyclic AMP. The following PTH fragments are useful as inhibitors of parathyroid hormone both in vivo and in vitro: [L-Tyr-34] bPTH (4-34) amide, [L-Tyr-34] bPTH (5-34) amide, [L-Tyr-34] bPTH (6-34) amide, [L-Tyr-34] bPTH (7-34) amide, [D-Tyr-34] bPTH (4-34) amide, [D-Tyr-34] bPTH (5-34) amide, [D-Tyr-34] bPTH (6-34) amide, [D-Tyr-34] bPTH (7-34) amide, [Nle-8, Nle-18, Tyr-34] bPTH (4-34) amide, [L-Tyr-34] hPTH (4-34) amide, [L-Tyr-34] hPTH (5-34) amide, [L-Tyr-34] hPTH (6-34) amide, [L-Tyr-34] hPTH (7-34) amide, [D-Tyr-34] hPTH (4-34) amide, [D-Tyr-34] hPTH (5-34) amide, [D-Tyr-34] hPTH (6-34) amide, [D-Tyr-34] hPTH (7-34) amide, [Nle-8, Nle-18, Try-34] hPTH (4-34) amide.

Other peptide hormone analogues can be constructed using the principles defined for PTH including the synthesis of analogues containing only a fragment of the corresponding natural peptide hormone. The following is a partial list of the peptide hormones to which the corresponding analogues can be synthesized: follicle stimulating hormone, luteinizing hormone, prolactin, growth hormone, thyroid stimulating hormone, adrenal corticotropin, melanocyte stimulating hormone, calcitonin, relaxin, vasopressin oxytocin, insulin, glucagon, erythropoietin, cholecystokinin, gastrin, angiotensin, gonadotropin releasing hormone, corticotropin releasing hormone; growth hormone releasing hormone; thyrotropin releasing hormone; prolactin releasing hormone; melanocyte stimulating hormone releasing hormone; growth hormone release inhibiting hormone; somatostatin, prolactin release inhibiting hormone, melanocyte stimulating hormone release inhibiting hormone, gonadocrinin, gonadostatin, and somatomedin.

II.

Use of Peptide Hormone Inhibitors

Peptide hormone analogues when administered to a vertebrate, such as mammals, fish or birds, blocks the endrocrine activity of the peptide hormone or other analogous molecules. This blockage occurs due to the affinity of the hormone analogue for the cell surface receptor. Administration of the peptide hormone analogue results in a binding to the cell surface receptor thereby preventing the binding of the natural hormone. Therefore, the peptide hormone analogue functions as a competitor with the naturally occurring hormone. The hormone analogue structure, while retaining high affinity for the hormone receptor, does not have the capacity to stimulate the production of second messenger molecules such as cyclic AMP, cyclic GMP, calcium ions or other second messenger molecules.

This method of inhibiting the action of peptide hormones comprises the administration of a therapeutically effective amount of any peptide hormone or analogue wherein the three N-terminal amino acids are removed and zero or more of the next four N-terminal amino acids are removed sequentially from the N-terminus. These hormone analogues retain specificity for the cell surface receptor without stimulating a physiological response. This method of use applies to the entire peptide hormone or its analogue, or to a fragment of the peptide hormone containing the receptor binding site.

The use of peptide hormone analogues is exemplified by parathyroid hormone analogues. The parathyroid hormone may be of bovine, human, or any vertebrate origin. The analogue may contain all the amino acids except for the modified N-terminal region or it might comprise the N-terminal 34 amino acids. Individual amino acids can be substituted to improve stability as exemplified by norleucine in the present invention.

The peptide hormone analogues of this invention can be used in vitro to measure the concentration of naturally occurring peptide hormone. This bioassay procedure is illustrated by a bioassay for parathyroid hormone. The unknown concentration of parathyroid hormone in a solution can be determined by measuring the amount of parathyroid hormone analogue required to inhibit its binding to the parathyroid hormone cell surface receptor. The concentration of PTH analogue required to block the action of parathyroid hormone is a direct indicator of the parathyroid hormone concentration.

Parathyroid hormone analogues can be used to diagnose the etiology of or to treat hypercalcemia through the administration of a therapeutically effective amount of the parathyroid hormone analogues of this invention. Similarly, other aspects of hyperparathyroidism, such as a hypercalcemic crisis, renal failure or hypertension can be treated through the administration of the parathyroid hormone analogues of this invention.

Tumors and other aberrant cell growth often produce hormone like substances causing a disease state. The use of peptide hormone analogues to block stimulation caused by such hormone like substances can result in the alleviation of the disease state. Therefore, the peptide hormone analogues of the present invention can be administered to treat diseases caused by aberrant production of hormone like substances.

Immune diseases such as inflammation, allergic responses and hyperactive lympocytes can be treated through the administration of peptide hormone analogues which block the action of peptide hormones, such as PTH analogues inhibiting the binding of PTH to cells of the immune system.

The peptide hormone analogues of this invention exhibit both oral and parenteral activity and can be formulated in dosage forms for oral parenteral, rectal, intra-nasal, or topical administration. Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluent. In the case of capsules, tablets, and pills, the dosage forms may also comprise buffering agents. Tablets and pills can additionally be prepared with an enteric coating.

Liquid dosage forms for oral administration include pharmaceutically acceptable emulsion, solutions, suspensions, syrups and elixers containing inert diluents commonly used in the pharmaceutical art. Besides inert diluents, such compositions can also include adjuvants, such as wetting agents, emulsifying and suspending agents, and sweetening. Preparations according to this invention for parenteral administration include sterile aqueous or non-aqueous solutions, suspensions or emulsions. Examples of non-aqueous solvents or vehicles are propylene glycol, polyethylene glycol, vegetable oils such as olive oil and injectable organic esters such as ethyloleate.

Compositions for rectal administration are suppositories which may contain in addition to the active substance, expients such as cocoa butter or a suppository wax. The dosage of active ingredient in the compositions of this invention may be varied; however it is necessary the amount of the active ingredient shall be such that a suitable dosage form is obtained. The selected dosage form depends upon the desired therapeutic effect, on the route on the administration, and on the duration of the treatment.

Obviously, numerous modifications and variations of the present invention are possible in light of the above teachings. It is therefore to be understood that within the scope of the appended claims, the invention may be practiced otherwise than as specifically described herein.

EXAMPLES

Example 1

Synthesis and Purification of Peptide Hormone Analogues of bPTH

Analogues of bovine parathyroid hormone, were prepared by a modification of the solid-phase method of Merrifield. Syntheses were preformed using a Beckman Model 990 Automated Synthesizer. Benzhydrylamine hydrochloride resin (polystyrene-1% by divinylbenzene, Beckman) was employed as the solid support in order to effect the carboxyamide ($CONH_2$) COOH-terminal modification.

The tertiary butyloxycarbonyl (Boc) group was used to protect the α-amino group of each amino acid during coupling, except arginine, which was protected by the amyloxycarbonyl group. Side-function protection was afforded as follows: (a) the hydroxyl group of serine was protected as the O-benzyl ether; (b) the hydroxyl group of tryosine as the 0-2,6-dichlorobenzyl ether; (c) the carboxyl group of aspartic acid as the benzyl ester; and (d) the imidazole nitrogen of histidine and the guanidine function of arginine were protected by the p-toluenesulfonyl group (protected histidine was stored as the dicyclohexylamine salt, and desalted immediately before use). All amino acids were obtained from Beckman Instruments, Peninsula Laboratories, or Bachem Chemicals.

The first amino acid, tryosine, was coupled to the copolymer resin by the following procedure. Five grams of copolymer resin (containing 0.52 meq $NH_2$/g), was washed (6x) with methylene chloride (freshly distilled over potassium carbonate), followed by pre-treatment (1.5 min, 2x) and then treatment (30 min) with 30% (v/v) trifluoroacetic acid (Pierce) in methylene chloride (6x). The resulting trifluoroacetate salt was neutralized by pre-washing (1.5 min. 2x) followed by treatment (10 min) with 10% (v/v) triethylamine (Pierce) in methylene chloride, followed by washing with methylene chloride (4x). The peptide bond was formed by the addition of a 2.5-molar ratio of Boc-0-2,6-dichlorobenzyl tyrosine and a 2.5-molar ratio of dicyclohexylcarbodiimide in methylene chloride to the reaction vessel. After the mixture was stirred (1 h), the amino acid-copolymer resin complex was washed to free it of the reagents of coupling with methylene chloride (6x). Subsequent amino acids were similarly incorporated with the exception of asparagine and glutamine, which were incorporated by the "active ester" method. For these amino acids, a 5-molar excess of the p-nitrophenyl "active ester" in dimethylformamide (DMF) was added and allowed to react overnight.

After incorporation of tryptophan at position 23, 1% mercaptoethanol was added to the trifluoroacetic acid reagent and to the methylene chloride wash cycle in all subsequent steps to minimize oxidation. Completeness of coupling was assessed qualitatively by the fluorescamine test. Triple coupling was required for isoleucine at position 5. Acetylation (2.5 ml of acetic anhydride and 0.75 ml of triethylamine in 25 ml of dimethylformamide, 15 min, 2x) was performed after a single coupling of tyrosine at the COOH-terminus, and after double coupling of histidine at position 32, in order to obtain a negative fluorescamine test. This pattern of repeat couplings was used during the synthesis of [Tyr-34]bPTH-(1-34)amide, and in addition repeat coupling was required for aspartic acid at position 30 and lysine at 27, but not required for isoleucine at 5. For the shorter peptide hormone analogues the last 3-7 amino acids were not coupled. D-amino acids can be inserted when desired in place of L-amino acids.

The peptide was cleaved from the copolymer resin with simultaneous removal of the side-chain protecting groups using an excess of twice-distilled, anhydrous hydrogen fluoride (HF) at 0° C. for 1 h in the presence of 3.5 ml of distilled anisole/2.5 g peptide-resin complex. Hydrogen fluoride was then removed by distillation under reduced pressure (oil vacuum pump). The peptide-resin mixture was washed with anhydrous ether to remove anisole. The peptide was then extracted by alternate washes of glacial acetic acid and water (4x each). The washes were combined and lyophilized to yield the crude peptide.

Crude peptide was purified initially by gel filtration on a Bio-Gel P-6 (Bio-Rad Laboratories) column (5.0×100 cm) and eluted with 1 M acetic acid. After lyophilization, the partially purified peptide was applied to a carboxymethylcellulose (CM-52, Whatman) ion-exchange column (1.2×15 cm). An LKB Ultragrad apparatus created a shallow-sloped conductivity gradient of ammonium acetate from 1.5 mmho (pH 5.1) to 20.0 mmho (pH 6.2).

Analysis of Synthetic Products

Multiple amino acid analyses were performed after acid hydrolysis in 5.7 N HCl at 110° C. in an evacuated desiccator for 24 h in the presence of 1/2000 (v/v) mercaptoethanol. Amino acid analyses were carried out using a Beckman Model 121M Analyzer. Automated Edman sequence analysis was performed to detect deletion-containing error peptides using a Beckman 890C Sequencer employing the single-coupling, double-cleavage method of Edman and Begg. Manual Edman degradations were performed and phenylthiohydantoin derivatives of amino acids were identified by thin-layer chromatography on silica-gel plates (Analtech) and by gas-liquid chromatography using a two-column system (10% D-560 and 1.5% AN-600).

Peptide homogeneity was assessed in multiple systems. Thin-layer chromatgraphy was conducted in two systems. System A: butanol/pyridine/acetic acid/water 15/10/3/12, 100-μm cellulose-coated plates (Brinkman Instruments), ninhydrin-staining; and system B: chloroform/methanol/35% (w/v) ammonium hydroxide, 2/2/1, 250-μm silica-gel-coated plates (Analtech), ninhydrin-staining. Thin-layer electrophoresis on 100-μm cellulose plates was performed at 600 volts in two solvent systems of pyridine/acetic acid/water in ratios of: (A) 1/10/289, pH 3.4; and (B) 30/1/270, pH 6.5. Analytic and preparative high pressure liquid chromatography (HPLC) using C-18 columns and elvant gradients of acetonitrile/water/0.1% trifluoroacetic acid were also used.

Synthesis and Purification

After hydrogen fluoride cleavage, 1.84 g of crude [Tyr-34]pBTH-(1-34)amide was obtained.

Analytical Evaluation

The peptides were demonstrated to be homogeneous and to conform to theoretical composition. In addition, [Try-34]bPTH-(1-34)amide was assessed by Edman sequence analysis and found to contain less than 6% deletion-containing error peptides. The peptides gave only a single spot in both thin-layer chromatography systems: $R_f$ values in Systems A and B were (0.59,0.86) for [Try-34]bPTH-(1-34)amide.

Amino acid content conformed to theoretical expectations. After HPLC purification, peptide analogues are homogeneous by HPLC criteria. Edman sequence analysis was performed to quantitate contamination by deletion-containing error peptides. Each cycle of Edman degradation quantitates the amino acids present at a given position in the peptide. Should a fraction of the synthetic product contain a deletional error, such an error would be detected as a "preview" of the amino acid expected at the next cycle of degradation. Sequence analysis of one of the analogues, [Try-34]bPTH-(1-34)amide was performed and yielded alanine at cycle 1, with <1% preview of the valine at position 2. "Preview" remained below the 6% level through 11 cycles (leucine, position 11) of Edman degradation; beyond this point, severe extractive losses prevented further analysis. Hence, the purified [Try-34]bPTH-(1-34)amide may contain as little as 6% contamination by deletion-containing error peptides.

EXAMPLE 2

In Vivo Administration of PTH Analogues as Inhibitors of PTH

The compound [Tyr-34]bPTH(7-34)amide was administered in vivo as an inhibitor of PTH stimulated biological activities. The effectivenss of the treatment was measured by measuring the urinary phosphate and cyclic AMP, standard procedures well known in endocrinology as valid measure of PTH activity. The dosage of PTH analogues used varied from more than 3.0 μg/Kg/hr to less than 15 mg/Kg/hr, optimally between 0.3 mg/Kg/hr and 1.5 mg/Kg/hr. Single bolus dosages were occassionally utilized as indicated containing the equivalent of many hours of the infusion procedure.

Procedure

Male weanling Holtzman rats were maintained on a purified vitamin D deficient diet containing 0.44% calcium and 0.30% phosphorous for 7 weeks. At this time, the rats weighed 130-170 g. Thyroparathyroidectomy of the vitamin D deficient rats was preformed under anesthesia with ketamin hydrochloride injected intratraperitoneally. The femoral vein was cannulated with a heparin-treated polyethylene tube, and the blood was collected via the catheter for determination of blood chemistries. When needed both femoral veins were cannulated. A polyethylene catheter was also inserted into the urinary bladder via the ventral approach. Each animal was fixed in a Ballman cage in a plastic chamber controlled at 24° C. All these surgical procedures were completed in about 40 minutes. A solution containing 7.5 mM calcium chloride, 5 mM magnesium chloride, 20 mM sodium chloride, 2.5 mM potassium chloride, and 4% glucose was immediately infused into the cannulated femoral veins. In addition, graded amounts of parathyroid hormone or its analogues were constantly infused into the rats starting 21 hours after the surgery.

Results

The PTH analogue [Tyr-34]bPTH(7-34)amide was a potent competitive antagonist of native PTH and lacked agonist activity. When the analogue was infused I.V. at 50-200 fold higher dose rate than the PTH, the analogue caused nearly complete inhibition of the PTH-mediated effects. No agonist properties were observed. Because the rats were sustained by calcium infusion, effects on calcium flux were not assessed.

Figure 1:
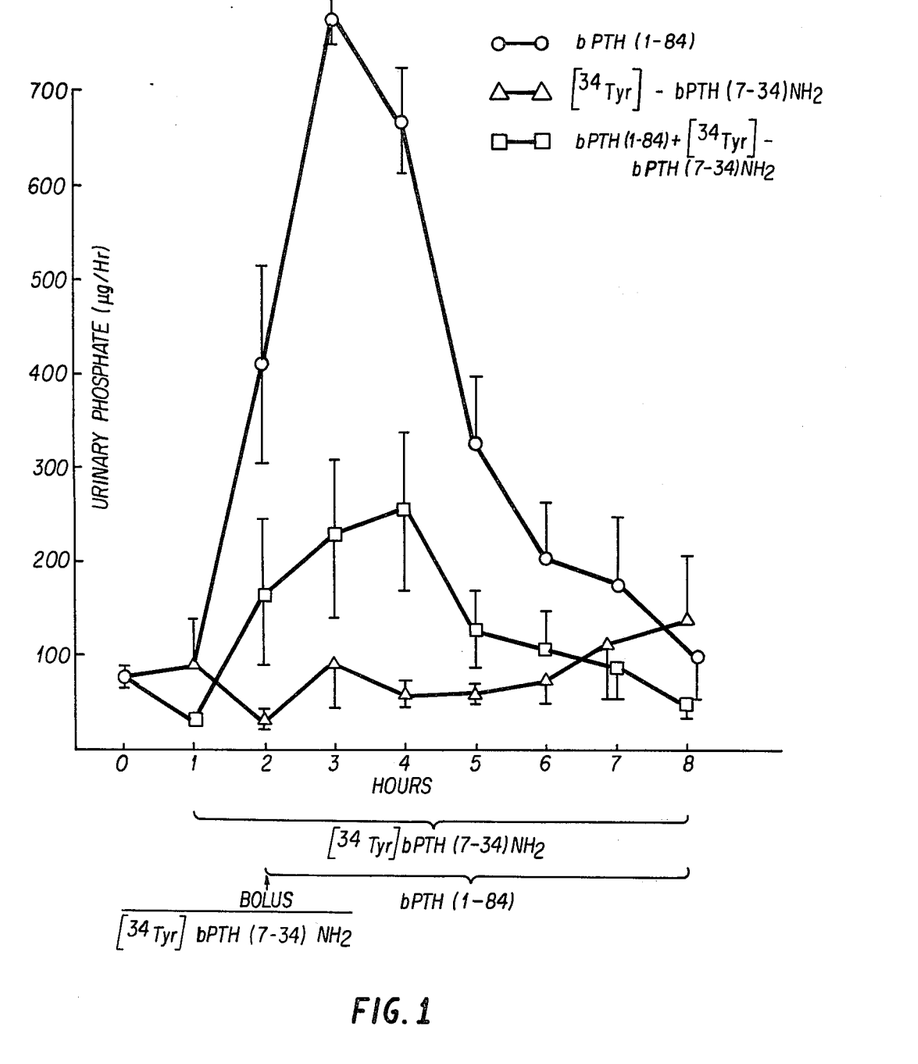
FIG. 1—Urinary phosphate as a function of time following infusion of bovine parathyroid hormone or analogues as indicated.

In FIG. 1, urinary phosphate in micrograms per hour, was measured as a function of hours following treatment with parathyroid hormone analogues as indicated in FIG. 1. At one hour, an infusion of the 7-34 analogue is begun intraveniously at 13.5 nanomoles per hour. This infusion is made continuously for the next 7 hours. At 2 hours, a bolus of the 7-34 analogue is given, and at the same time a continuous infusion of 0.27 of native parathyroid hormone, is begun and continued for the next 6 hours. In FIG. 1, the uppermost line depicts infusion of the native PTH alone with a peak of phosphaturia occurring 3 to 4 hours into the experiment. When the 7-34 analogue alone is infused, it has no stimulatory effect on urinary phosphate production as demonstrated in the bottom line of FIG. 1. The middle line is the curve generated for co-infusion of both the intact PTH and the 7-34 analogue. As can be seen, there is a marked inhibition of the parathyroid hormone-stimulated urinary phosphate production at 3 to 4 hours and actually at all time points for which data has been obtained. Therefore, the PTH (7-34) analogue is an effective inhibitor of the action of parathyroid hormone in vivo.

Figure 2:
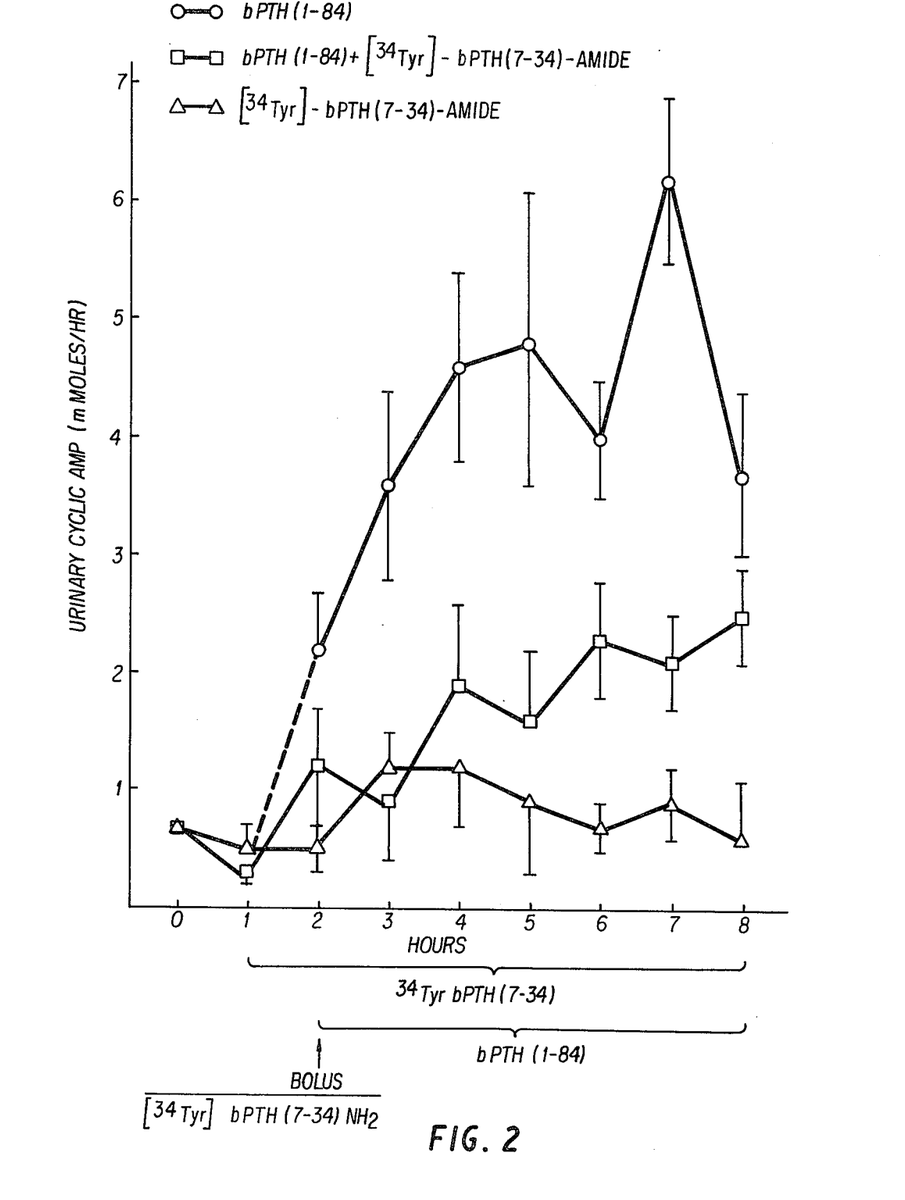
FIG. 2—Urinary cyclic adenosine monophosphate as a function of time following infusion of bovine parathyroid hormone or analogues as indicated.

FIG. 2 is an experiment identical to that shown in FIG. 1, however, urinary cyclic AMP is now measured instead of urinary phosphate. Again, the 7-34 analogue on the bottom line has no agonist-like effect when administered alone. The native parathyroid hormone has a marked effect on urine cyclic AMP production as demonstrated in the top line, and co-infusion of both native parathyroid hormone and the 7-34 analogue results in marked inhibition of urine cyclic AMP excretion as shown in the middle line. Therefore, the PTH analogue is demonstrated to be an effective inhibitor of PTH stimulated cyclic AMP excretion in the urine.

Figure 3:
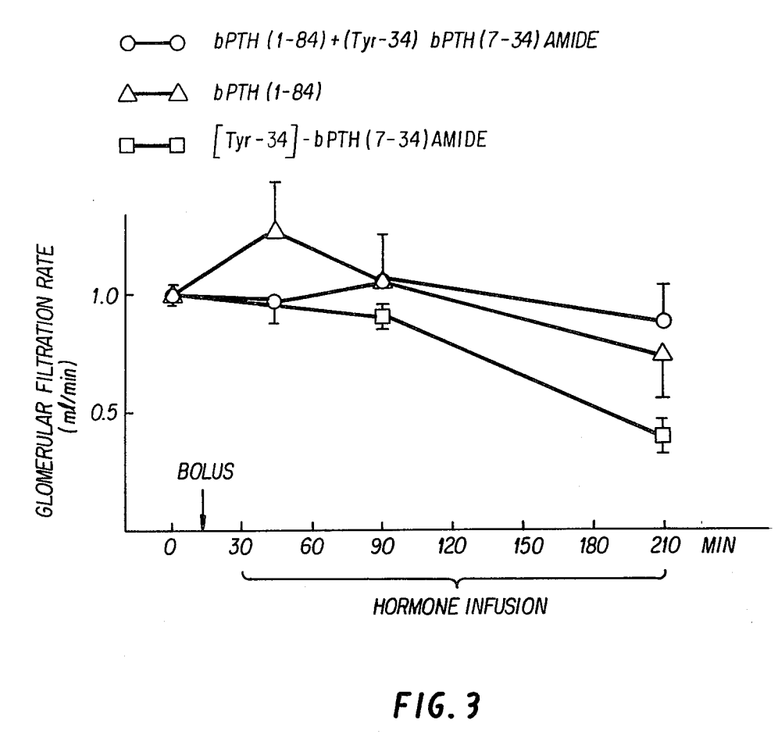
FIG. 3—Glomerular filtration rate as a function of time following infusion of bovine parathyroid hormone or its analogues as indicated.
Figure 4:
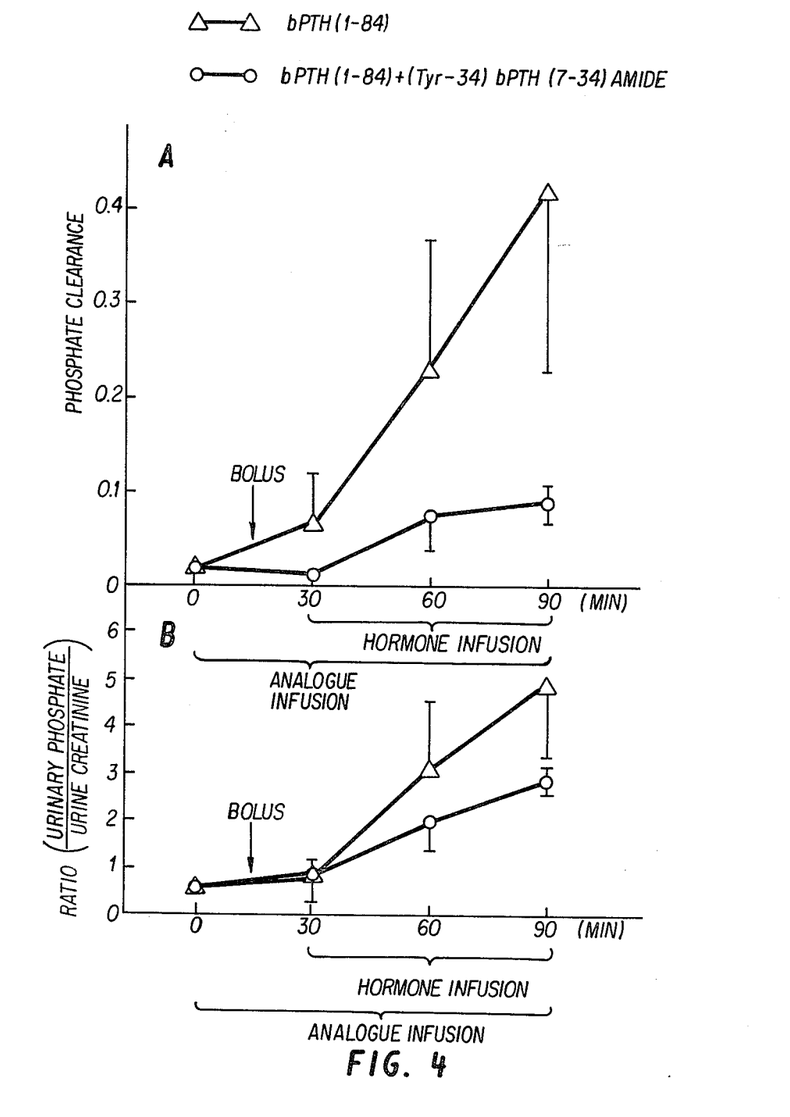
FIG. 4—Inhibition of phosphate clearance (PANEL A) and ratio (urinary phosphate/urinary creatinine) (PANEL B) as a function of time following infusion of bovine parathyroid hormone or its analogues as illustrated.

The glomerular filtration rate in FIG. 3 demonstrates the volume of urine produced per unit time. The top line is that for native parathyroid hormone and the bottom line is for co-infusion of the native PTH and the 7-34 analogue as shown in the drawing. In FIG. 4 the phosphate clearance is demonstrated formally (Panel A) and through measuring the ratio of urinary phosphate to urinary creatine (Panel B). This ratio allows correction for fluxuations in urinary volume. As can be seen in FIG. 4, the analogue severely decreases the amount of phosphate found in the urine indicating significant inhibition of the in vivo activity of the parathyroid hormone.

Figure 5:
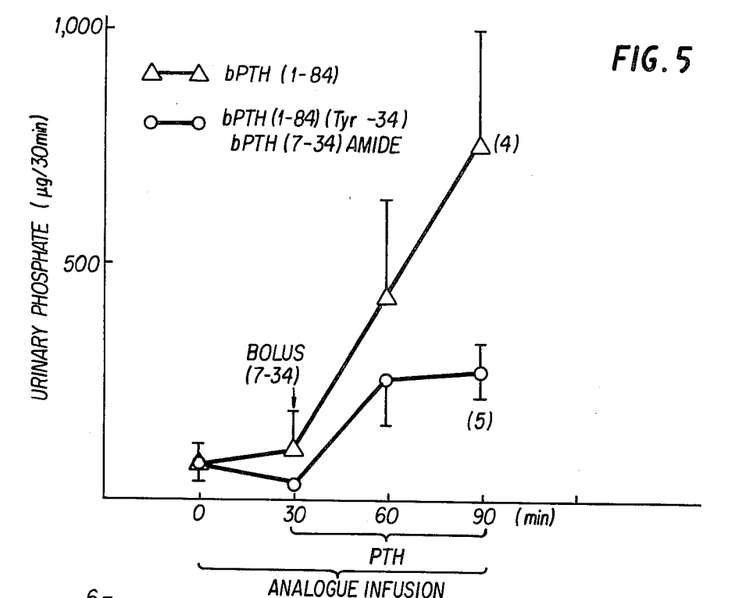
FIG. 5—Urinary phosphate excretion as a function of time following administration of bovine parathyroid hormone or its analogues as illustrated.
Figure 6:
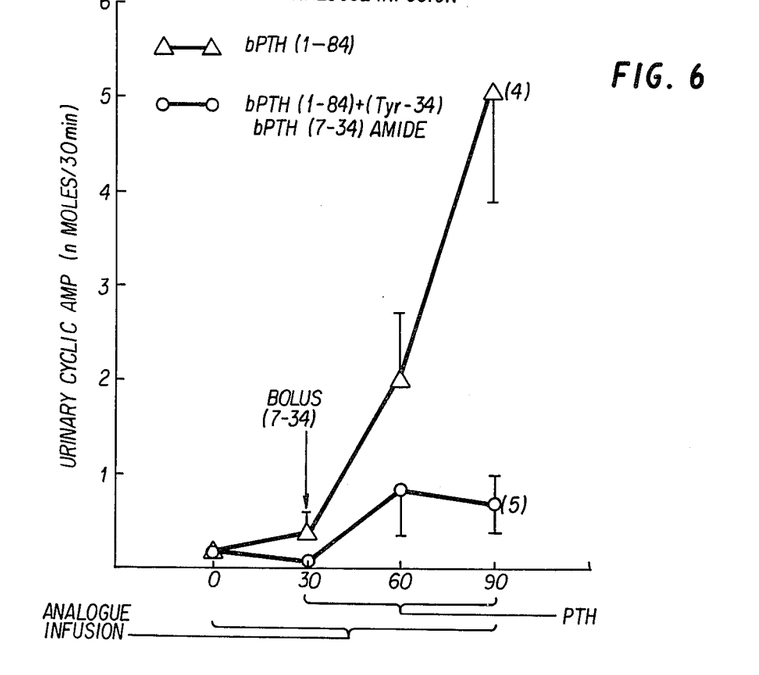
FIG. 6—Urinary cyclic adenosine monophosphate production as a function of time following infusion of bovine parathyroid hormone or its analogues as illustrated.

FIG. 6 shows the urinary cyclic AMP production during the same experiment diagrammed in FIG. 5. Again, the production of cyclic AMP is severely inhibited by infusion of the 7-34 analogue. In the case of this experiment, the analogue was infused for ½ hour prior to the beginning of the infusion of native PTH at time 30 minutes. At the beginning of the native hormone infusion (30 minutes) a bolus of the 7-34 is given.

Figure 7:
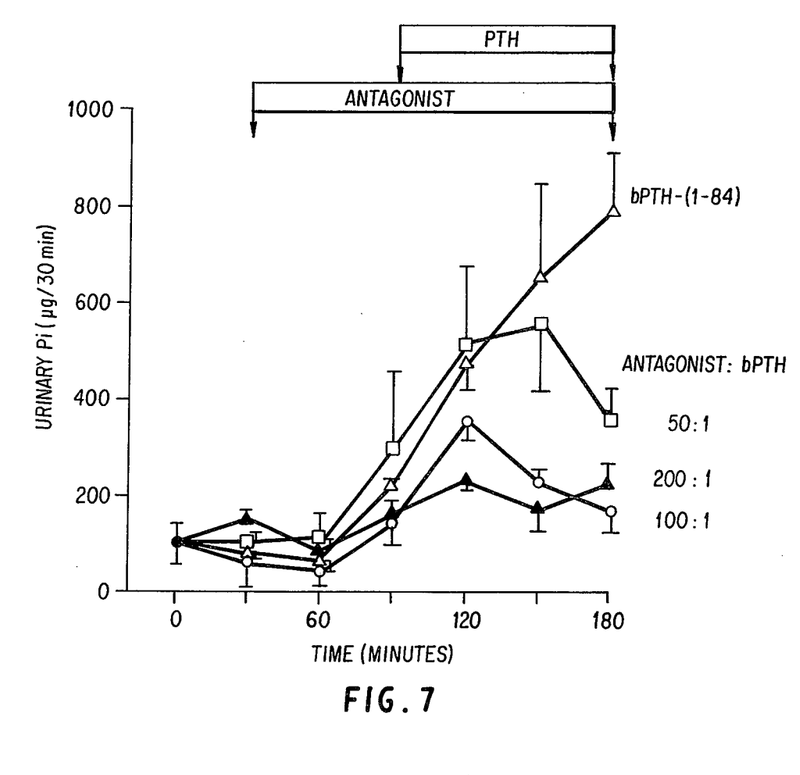
FIG. 7—A dose response curve for the inhibitory activity of the bovine parathyroid hormone analogue [Tyr-34] bPTH (7-34).
Figure 8:
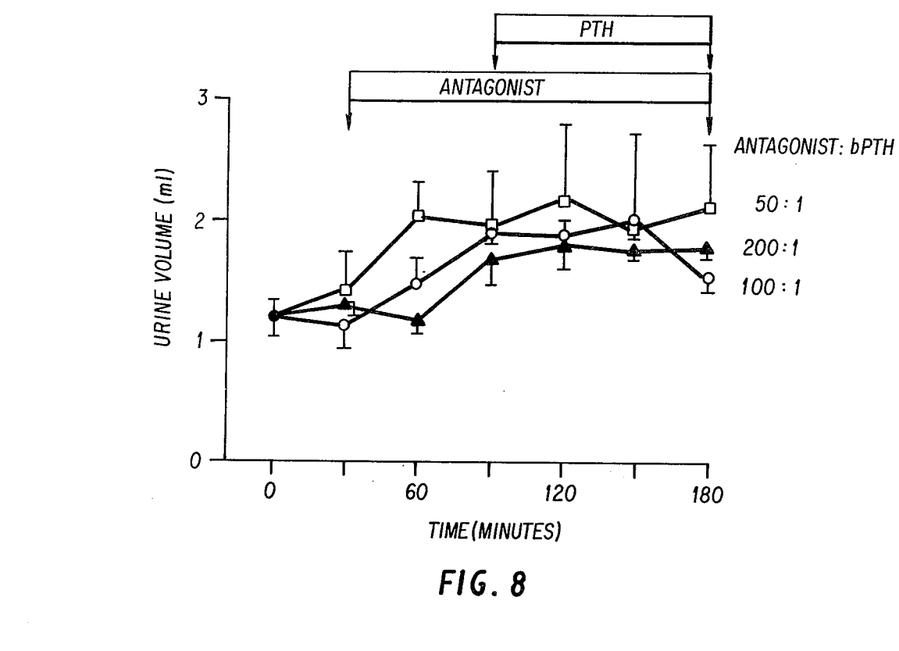
FIG. 8—Urine volume released as a function of time following the administration of bovine parathyroid hormone or its analogues as illustrated.

A dose response curve for the inhibitory activity of the 7-34 analogue is illustrated in FIG. 7. Urinary phosphate excretion is plotted on the vertical axis and time in minutes is plotted on the horizontal axis. A control period of 30 minutes is established at the beginning of the experiment. At 30 minutes a continuous infusion of the 7-34 analogue is begun at a dose rate of 0, 13.5, 27, or 54 nanamoles per hour. These values correspond to a molar-dose rate of infusion of 0-fold, 50-fold, 100-fold, or 200-fold moles of inhibitor to moles of native parathyroid hormone. The native parathyroid hormone is infused continuously beginning at 90 minutes (or 1 hour after the beginning of the 7-34 infusion). The top lines (triangles) show infusion of native parathyroid hormone alone. The next line down (squares) shows the co-infusion of the 50-fold excess administered through a separate intravenous line. The circles line depicts a 100:1 ratio. The bottom line (filled triangles) corresponds to a 200-fold excess of inhibitor. There is a progressive inhibition of parathyroid hormone-stimulated phosphate excretion with increasing doses of the inhibitor. Somewhere between a 100-fold to 200-fold molar dose ratio is required to cause complete inhibition of parathyroid hormone-stimulated phosphate excretion. At a dose of 50-fold, approximately 50% inhibition occurs.

What is claimed as new or desired to be secured by Letters Patent of the United States is:

1. A parathyroid hormone analogue, comprising: a parathyroid peptide fragment wherein the three N-terminal amino acids and zero or more of the next four N-terminal amino acids are absent from a parathyroid hormone (PTH), from a parathyroid hormone fragment comprising at least the first 34 amino acids of said PTH, or from said parathyroid hormone or said parathyroid hormone fragment in which amino acid #34 is replaced with D- or L-tyrosine or in which amino acids #8 and #18 are each replaced with norleucine and amino acid #34 is replaced with D- or L-tyrosine, wherein the carboxy-terminal of said peptide fragment is optionally an amide, and wherein the N-terminal of said peptide fragment is optionally a D-amino acid.

2. The analogue of claim 1 wherein said PTH is bovine PTH (bPTH).

3. The analogue of claim 2 wherein said hormone fragment comprises amino acids 1-34 (bPTH (1-34)).

4. The analogue of claim 2 or 3 wherein amino acid #34 is replaced by either D- or L-tyrosine.

5. The analogue of claim 2 or 3 wherein the N-terminal amino acid of said peptide fragment is a D-amino acid.

6. The analogue of claim 2 or 3 wherein the carboxy-terminal amino acid of said peptide fragment is an amide.

7. The analogue of claim 1 wherein said analogue is [L-Tyr-34] bPTH (4-34) amide.

8. The analogue of claim 1 wherein said analogue is [L-Tyr-34] bPTH (5-34) amide.

9. The analogue of claim 1 wherein said analogue is [L-Tyr-34] bPTH (6-34) amide.

10. The analogue of claim 1 wherein said analogue is [L-Tyr-34] bPTH (7-34) amide.

11. The analogue of claim 1 wherein said analogue is [D-Tyr-34] bPTH (4-34) amide.

12. The analogue of claim 1 wherein said analogue is [D-Tyr-34] bPTH (5-34) amide.

13. The analogue of claim 1 wherein said analogue is [D-Tyr-34] bPTH (6-34) amide.

14. The analogue of claim 1 wherein said analogue is [D-Tyr-34] bPTH (7-34) amide.

15. The analogue of claim 1 wherein said analogue is [Nle-8, Nle-18, Tyr-34] bPTH (4-34) amide.

16. The analogue of claim 1 wherein said PTH is human PTH (hPTH).

17. The analogue of claim 16 wherein said hormone fragment comprises amino acids 1-34 (hPTH (1-34)).

18. The analogue of claim 16 or 17 wherein amino acid #34 is replaced by either D- or L-tyrosine.

19. The analogue of claim 16 or 17 wherein the N-terminal amino acid of said peptide fragment is a d-amino acid.

20. The analogue of claim 16 or 17 wherein the carboxy-terminal amino acid of said peptide fragment is an amide.

21. The analogue of claim 16 wherein said analogue is [L-Tyr-34] hPTH (4-34) amide.

22. The analogue of claim 16 wherein said analogue is [L-Tyr-34] hPTH (5-34) amide.

23. The analogue of claim 16 wherein said analogue is [L-Tyr-34] hPTH (6-34) amide.

24. The analogue of claim 16 wherein said analogue is [L-Tyr-34] hPTH (7-34) amide.

25. The analogue of claim 16 wherein said analogue is [D-Tyr-34] hPTH (4-34) amide.

26. The analogue of claim 16 wherein said analogue is [D-Tyr-34] hPTH (5-34) amide.

27. The analogue of claim 16 wherein said analogue is [D-Tyr-34] hPTH (6-34) amide.

28. The analogue of claim 16 wherein said analogue is [D-Tyr-34] hPTH (7-34) amide.

29. The analogue of claim 16 wherein said analogue is [Nl3-8, Nle-18, Tyr-34] hPTH (4-34) amide.

30. A method of inhibiting the action of parathyroid hormone, comprising:
administering a therapeutically effective amount of an analogue of claim 1 to a vertebrate.

31. The method of claim 30 wherein said hormone is bPTH.

32. The method of claim 30 wherein said hormone is hPTH.

33. The method of claim 30, wherein said hormone fragment comprises the N-terminal 34 amino acids of a parathyroid hormone.

34. The method of claim 33 wherein said hormone fragment comprises the N-terminal 34 amino acids of bPTH.

35. The method of claim 33 wherein said hormone fragment comprises the N-terminal 34 amino acids of hPTH.

36. The method of claim 30 wherein said peptide fragment is [L-Tyr-34] bPTH (4-34) amide.

37. The method of claim 30 wherein said peptide fragment is [L-Tyr-34] bPTH (5-34) amide.

38. The method of claim 30 wherein said peptide fragment is [L-Tyr-34] bPTH (6-34) amide.

39. The method of claim 30 wherein said peptide fragment is [L-Tyr-34] bPTH (7-34) amide.

40. The method of claim 30 wherein said peptide fragment is [D-Tyr-34] bPTH (4-34) amide.

41. The method of claim 30 wherein said peptide fragment is [D-Tyr-34] bPTH (5-34) amide.

42. The method of claim 30 wherein said peptide fragment is [D-Tyr-34] bPTH (6-34) amide.

43. The method of claim 30 wherein said peptide fragment is [D-Tyr-34] bPTH (7-34) amide.

44. The method of claim 30 wherein said peptide fragment is [Nle-8, Nle-18, Tyr-34] bPTH (4-34) amide.

45. The method of claim 30 wherein said peptide fragment is [L-Tyr-34] hPTH (4-34) amide.

46. The method of claim 30 wherein said peptide fragment is [L-Tyr-34] hPTH (5-34) amide.

47. The method of claim 30 wherein said peptide fragment is [L-Tyr-34] hPTH (6-34) amide.

48. The method of claim 30 wherein said peptide fragment is [L-Tyr-34] hPTH (7-34) amide.

49. The method of claim 30 wherein said peptide fragment is [L-Tyr-34] hPTH (4-34) amide.

50. The method of claim 30 wherein said peptide fragment is [L-Tyr-34] hPTH (5-34) amide.

51. The method of claim 30 wherein said peptide fragment is [L-Tyr-34] hPTH (6-34) amide.

52. The method of claim 30 wherein said peptide fragment is [L-Tyr-34] hPTH (7-34) amide.

53. The method of claim 30 wherein said peptide fragment is [Nle-8, Nle-18, Tyr-34] hPTH (4-34) amide.

54. An in vitro bioassy of parathyroid hormone, wherein a measured amount of the analogue of claim 1 inhibits binding a parathyroid hormone to a PTH receptor in vitro.

55. The method of claim 30, wherein said administering is for the treatment of hypercalcemia.

56. The method of claim 30, wherein said administering is for the diagnosing or treating of hyperparathyroidism.

57. The method of claim 56, wherein the hyperparathyroidism results in a hypercalcemic crisis.

58. The method of claim 56, wherein the hyperparathyroidism results in renal failure.

59. The method of claim 56, wherein a tumor produces a parathyroid hormone-like substance.

60. The method of claim 30, wherein said administering is for the treatment of an immune disease.

61. The method of claim 60, wherein the immune disease comprises inflammation.

62. The method of claim 60, wherein the immune disease comprises an allergic response.

63. The method of claim 60, wherein the immune disease comprises hyperactive lymphocytes.

64. The method of claim 30, wherein said administering is for the treatment of hypertension.

* * * * *